United States Patent
Wong

(10) Patent No.: US 9,773,361 B2
(45) Date of Patent: Sep. 26, 2017

(54) SYSTEM AND METHOD FOR CROSS-CONTAMINATION PREVENTION

(71) Applicant: SCHNEIDER ELECTRIC BUILDINGS, LLC, Palatine, IL (US)

(72) Inventor: Lian Khong Wong, Flower Mound, TX (US)

(73) Assignee: SCHNEIDER ELECTRIC BUILDINGS, LLC, Palatine, IL (US)

( * ) Notice: Subject to any disclaimer, the term of this patent is extended or adjusted under 35 U.S.C. 154(b) by 0 days.

(21) Appl. No.: 14/653,763

(22) PCT Filed: Dec. 19, 2012

(86) PCT No.: PCT/US2012/070595
§ 371 (c)(1),
(2) Date: Jun. 18, 2015

(87) PCT Pub. No.: WO2014/098841
PCT Pub. Date: Jun. 26, 2014

(65) Prior Publication Data
US 2015/0332529 A1    Nov. 19, 2015

(51) Int. Cl.
*G07C 9/00* (2006.01)
*G06F 19/00* (2011.01)
(Continued)

(52) U.S. Cl.
CPC ..... *G07C 9/00031* (2013.01); *G06F 19/3406* (2013.01); *G07C 9/00166* (2013.01); *G07C 2209/04* (2013.01)

(58) Field of Classification Search
CPC .......... G07C 9/00; G06F 19/00; G06Q 40/00; G06N 5/02; G06K 19/00
(Continued)

(56) References Cited

U.S. PATENT DOCUMENTS 7,161,465 B2 *   1/2007   Wood .............. G06Q 10/10
                                             340/5.2
7,551,092 B1 *   6/2009   Henry ............ G08B 21/245
                                             340/286.07
(Continued)

FOREIGN PATENT DOCUMENTS

CN      101438297 A      5/2009
CN      201569885 U      9/2010
(Continued)

OTHER PUBLICATIONS

Extended European Search Report from corresponding PCT Application No. PCT/US2012/070595 dated Jul.-Nov. 2016.
(Continued)

*Primary Examiner* — Nam V Nguyen
(74) *Attorney, Agent, or Firm* — Lendo & Anastasi, LLP

(57) ABSTRACT

Cross-contamination prevention systems and cross-contamination prevention methods are provided for defining and automatically enforcing access restrictions between environments where cross-contamination may occur. The system and methods can evaluate a person's exposure to contaminants in one or more locations against contamination risk posed for another location. The system can prevent or allow access to the other location based on that evaluation. Some embodiments can be implemented in a laboratory setting and configured to prevent cross-contamination between different laboratories and/or experiments being conducted.

20 Claims, 5 Drawing Sheets

(51) Int. Cl.
*G06Q 40/00* (2012.01)
*G06N 5/02* (2006.01)
*G06K 19/00* (2006.01)
*H04K 1/00* (2006.01)
*G08B 21/00* (2006.01)

(58) Field of Classification Search
USPC .... 340/686.1, 539.12, 573.1, 5.2, 5.83, 541, 340/567, 572.1; 235/382, 382.5
See application file for complete search history.

(56) References Cited

U.S. PATENT DOCUMENTS

| | | | |
|---|---|---|---|
| 7,836,850 B2 | 11/2010 | Pratt | |
| 8,872,665 B2 * | 10/2014 | Snodgrass | G06F 19/327 340/573.1 |
| 9,245,437 B2 * | 1/2016 | Best | G08B 13/1427 |
| 2005/0004863 A1 | 1/2005 | Havrilak | |
| 2006/0102717 A1 | 5/2006 | Wood et al. | |
| 2007/0225995 A1 | 9/2007 | Moore | |
| 2012/0169458 A1 | 7/2012 | Dubois, Jr. et al. | |

FOREIGN PATENT DOCUMENTS

| | | |
|---|---|---|
| CN | 102238688 A | 11/2011 |
| GB | 2458118 A | 9/2009 |

OTHER PUBLICATIONS

International Search Report from corresponding PCT/US2012/070595 dated Feb. 27, 2013.

* cited by examiner

SYSTEM AND METHOD FOR CROSS-CONTAMINATION PREVENTION

This application is a U.S. National Stage Application under 35 U.S.C. §371 of International Application No. PCT/US2012/070595, filed Dec. 19, 2012, which is hereby incorporated by reference in its entirety for all purposes.

BACKGROUND

Technical Field

The technical field of this disclosure relates generally to access control systems and, more particularly, to systems and methods that automatically enforce access control to physical locations subject to cross-contamination risk.

Background Discussion

In various settings, scientists, technicians and personnel working, for example, in laboratory environments are exposed to various substances during the course of their work. Conventionally, lab personnel are required to track their own exposure to substances present in the lab to ensure that the contents of one lab do not contaminate any experiments being conducted in another lab. In some instances, lab personnel can be rigorously trained to avoid contamination between labs. In other settings, various procedures can be implemented to minimize cross-contamination risks. Such procedures can include the use of sterilization or wash down areas to remove any contaminants.

SUMMARY

It is realized that even the most rigorous training and detailed procedures can fail, particularly when personnel are inattentive, fatigued, or simply forgetful. At least some aspects and embodiments of a cross-contamination prevention system ("CCPS") provide for and automatically enforce access restrictions between physical environments where cross-contamination may occur. In one implementation, the system can evaluate a person's exposure to substances in one or more locations against contamination risk posed for another location. Further, according to other aspects, the system can prevent or allow access to the other location based on that evaluation. Some embodiments can be implemented in a laboratory setting and configured to prevent cross-contamination between different laboratories and/or experiments being conducted. Some other embodiments can be implemented in a hospital setting and configured to prevent cross-contamination between patients and prevent exposure to illnesses, among other options.

According to one embodiment, the CCPS may include security devices installed at entrances and exits of access points within a building, and may also include security control systems for operating the security devices. For example, the security control systems can be configured to identify a person seeking entrance, establish and/or verify the person's authority to enter an area, and further prevent access to unauthorized persons. Examples of security devices include locking mechanisms installed at access points and respective security input devices. The security input devices can accept an identification communication from the person (e.g., using a badge and a badge reader, swiping a card in a card reader, inputting security codes on a keypad, providing biometric input at a biometric sensor, etc.) and grant or deny access to a location based on authorizations defined for the identified person managed by the security control system. In other embodiments, the CCPS can be coupled with a security control system and receive identification, authorization, and/or prior location information from the security control system.

In some embodiments, the CCPS can be configured to restrict access to locations based on dynamic access control. In one example, the system's dynamic access control includes evaluations of access requests responsive to timing of the current request and/or based on locations that the requestor has visited prior to the current request. In some embodiments, each location within a laboratory environment can be associated with contamination restrictions. The contamination restrictions can be associated with substances that pose a contamination risk and can further include definition of lengths of time associated with a given exposure. The length of time can define how long a particular restriction should be enforced by the CCPS. In one example, the length of time establishes how long a person will be prevented from entering an area where a contamination risk is present. The contamination restrictions can also include specification of contamination risks between one or more contaminants. For example, the system can be configured to track contamination risk based on definition of contaminants present in a location.

According to one aspect, a system for cross-contamination prevention is provided. The system for cross-contamination comprises at least one processor operatively connected to a memory, the at least one processor when executing is configured to analyze an access request to a physical location, identify a contamination risk posed by permitting access to the physical location based on prior location information, and restrict access to the physical location in response to identifying the contamination risk.

In one embodiment, the system further comprises a storage subsystem configured to store contamination risks associated with a plurality of physical locations. In one embodiment, the storage subsystem is configured to associate information on at least one contamination risk with a person based on access to at least one of the plurality of physical locations. In one embodiment, the storage subsystem is configured to define a time period associated with a respective contamination risk.

In one embodiment, the system further comprises an access control subsystem configured to receive an access credential from a person seeking access to the physical location. In one embodiment, the at least one processor is configured to determine authorization to enter the physical location responsive to the access credential. In one embodiment, the at least one processor is configured to determine the prior location information associated with an access request responsive to receiving the access credential. In one embodiment, the at least one processor is configured to communicate a control message to the access control subsystem to restrict access to the physical location.

In one embodiment, identifying the contamination risk posed by permitting access includes changing one or more contamination risks responsive to access to a sterilization location. In one embodiment, identifying the contamination risk posed by permitting access includes changing one or more contamination risks responsive to a time period associated with a respective one of the one or more contamination risks.

According to one aspect, a method for cross-contamination prevention comprises analyzing, by a computer system, an access request to a physical location, identifying, by the computer system, a contamination risk posed by permitting access based on prior location information, and restricting, by the computer system, access to the physical location in response to identifying the contamination risk.

In one embodiment, the method further comprises storing, by the computer system, contamination risks associated with a plurality of physical locations. In one embodiment, the method further comprises associating information on at least one contamination risk with a person based on access to at least one of the plurality of physical locations. In one embodiment, the method further comprises defining a time period associated with a respective contamination risk. In one embodiment, the method further comprises receiving an access credential from a person seeking access to the physical location. In one embodiment, the method further comprises determining authorization to enter the physical location responsive to the access credential.

In one embodiment, the method further comprises determining the prior location information associated with an access request responsive to receiving the access credential. In one embodiment, identifying the contamination risk posed by permitting access includes changing one or more contamination risks responsive to access to a sterilization location. In one embodiment, identifying the contamination risk posed by permitting access includes changing one or more contamination risks based on a time period associated with a respective one of the one or more contamination risks.

According to one aspect, a non-transitory computer readable medium is provided. The non-transitory computer readable medium having stored thereon sequences of instruction for cross-contamination prevention including instructions that will cause at least one processor of a computer system to analyze an access request to a physical location, identify a contamination risk posed by permitting access based on prior location information; and restrict access to the physical location in response to identifying the contamination risk.

In one embodiment, the at least one processor is caused to store contamination risks associated with a plurality of physical locations. In one embodiment, the at least one processor is caused to associate information on at least one contamination risk with a person based on access to at least one of the plurality of physical locations. In one embodiment, the at least one processor is caused to define a time period associated with a respective contamination risk. In one embodiment, the at least one processor is caused to receive an access credential from a person seeking access to the physical location. In one embodiment, the at least one processor is caused to determine authorization to enter the physical location responsive to the access credential.

In one embodiment, the at least one processor is caused to determine the prior location information associated with an access request responsive to receiving the access credential. In one embodiment, identifying the contamination risk posed by permitting access includes changing one or more contamination risks responsive to access to a sterilization location. In one embodiment, identifying the contamination risk posed by permitting access includes changing one or more contamination risks based on a time period associated with a respective one of the one or more contamination risks.

Other aspects, embodiments and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Any embodiment disclosed herein may be combined with any other embodiment.

References to "an embodiment," "an example," "some embodiments," "some examples," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearances of such terms herein are not necessarily all referring to the same embodiment or example.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

Figure 1:
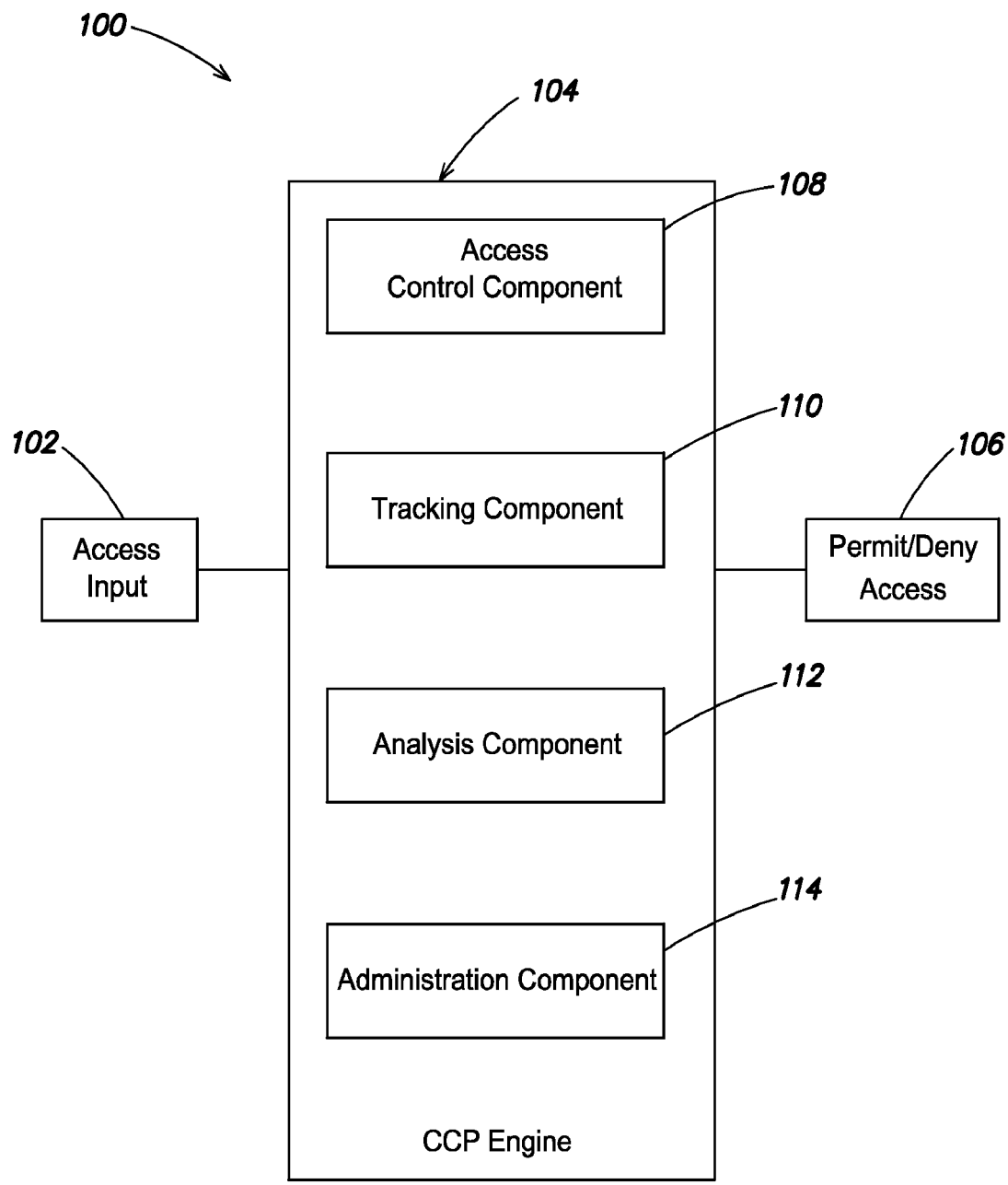
FIG. 1 is a block diagram of an example cross-contamination prevention system.

At least some embodiments disclosed herein include apparatus and processes for controlling access to one or more physical locations based on cross-contamination risk. In some embodiments, access to a location is prevented (e.g., regardless of authorization) based on a cross-contamination risk associated with historical location information. Cross-contamination risk can be determined by the system, based on contamination states associated with locations. For example, a user can specify in the system that a Lab A poses a contamination risk to Lab B. In another example, Lab A can be identified as a contamination risk to a plurality of other locations, and even all other locations in a building. The contamination risk can be associated with a period of time, beyond which the risk for contamination is minimal or non-existent. Each risk can then be associated with a person visiting a location for the period of time. In some examples, contamination risk is tracked in the system by changing the person's contamination state. In some embodiments, the system can be configured to identify when a person enters a location associated with a contamination risk and change their state accordingly.

In one embodiment, the person, responsive to entry, is associated with the contamination risk, for example, as a contamination state stored in a user profile. The risk or contamination state can be evaluated by the system to provide access control. In the above example, a person who visited Lab A can subsequently be prevented from accessing Lab B, even if the person is normally authorized to enter Lab B. In some embodiments, a user can clear an associated contamination state from their profile. For example, the user can visit a sterilization or wash down room. Responsive to an access request to the sterilization or wash down room, any contamination state associated with the user can be cleared by the system.

Examples of the methods and systems discussed herein are not limited in application to the details of construction and the arrangement of components set forth in the following description or illustrated in the accompanying drawings. The methods and systems are capable of implementation in other embodiments and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Cross-Contamination Prevention System

Some embodiments implement a cross-contamination prevention system that provides for and can automatically enforce access restrictions between physical locations where cross-contamination may occur. In some examples, the CCPS can be implemented in a laboratory setting where the materials used in experimentation in a respective lab need to be isolated from other materials. The CCPS can be especially beneficial in large laboratory settings, where multiple cross-contamination risks can exist, making individual compliance by personnel difficult at best.

FIG. 1 illustrates one embodiment of a CCPS 100. The CCPS 100 can be configured to monitor and control access to rooms within a building using a cross-contamination prevention ("CCP") engine 104. Elements of the system 100 can be provided using a computing system such as the computer system 500 and/or 502 described with reference to FIG. 5. For example, the CCP engine 104 can be executed on the computer system 500 and/or 502 to provide the functions and operations discussed herein. In other embodiments, the CCP engine 104 can include addition components executed on the computer system to perform specific operations. In some implementations, the CCPS 100 and/or CCP engine 104 can be configured to communicate with existing systems, for example, to augment access control provided by a security system and/or a building management system.

As shown in FIG. 1, the CCP engine 104 receives access input from an access control device 102. In some implementations, the access control device 102 can include magnetic card readers, RFID receivers, keypads, biometric sensors, video cameras, and any one or more of a variety of access control devices configured to receive an access credential from a person and identify the person requesting entry based on their access credential. In some examples, the access credential can be supplied from a mobile computing device, including a smart phone. The access control device 102 can be configured to receive the access credential, and supply the access credential to the CCP engine 104 for evaluation.

The CCP engine 104 can be configured to identify the person requesting entry based on their access credential. Further, the CCP engine 104 can include an access control component 108 that is configured to identify the person and determine authorization to enter a given location based on the person's identity. In some implementations, the CCP engine 104 can be configured to receive authorization/access permission from another system. For example, the access control component 108 can be configured to receive authorization information directly or indirectly from the other system (including e.g., security systems, building management systems, etc.). In response to granted access, the CCP engine 104 can be configured to track access to locations for each person in the system. Each access can be captured and stored for subsequent analysis.

In one example, an access control component 108 can be configured to record access requests and associate them with the person requesting access. In some embodiments, the CCP engine 104 can also be configured to track actual entry into a location, rather than the passing of the authorization check. In one example, actual access to the location can then be stored and used by the system to determine subsequent cross-contamination risk. In one embodiment, a user profile for the person accessing the location can be used to store access information. In other embodiments, the CCP engine 104 can include a tracking component 110 configured to track locations accessed by a person and associate accessed location(s) to a user profile.

Each location can be associated with a contamination risk stored on the system. For example, contamination risks can be defined using one to one relationships between locations, one to many relationships between locations, among other options. The system can also store information on location (s) having no contamination risk. In one alternative, locations having no contamination risks are not tracked in the system.

Stated broadly, according to one embodiment, the system 100 and/or CCP engine 104 can be configured to map a contamination risk posed by one location to any location that may be affected by the contamination. The mappings of risks can be associated with a person or even an object (e.g., tracked with an RFID) based on accessed locations. The association to the risk can be maintained until a time period expires or in some examples, until the person or object visits a wash down room configured to remove contaminants.

According to some embodiments, the CCP engine 104 can be configured to access tracked locations for a person to obtain contamination risk information. If the contamination risk is indicated for a new location, when the person attempts to access the new location, the CCP engine 104 can deny access by delivering a control communication 106. In one embodiment, the CCP engine 104 can be configured to provide an alert to the person denied access, detailing the reasons for denying access. An example alert can indicate what contaminant or location the person is associated with, and in another example, can include specification of a location of a wash down room to clear their contamination state.

In some embodiments, the CCP engine 104 can include an analysis component 112 configured to analyze location information for a person and determine any associated contamination risks. In other embodiments, contamination risks can also be stored in a user profile responsive to location information. The analysis component 112 can also be configured to access contamination risks in the user profile to grant or deny access to a location. Contamination risks defined on the system 100 can include a time period during which the contamination risk should be enforced. In one example, the time period for a contamination risk can be set as a number of minutes, a number of hours, days, and even weeks. The analysis component 112 can evaluate the time associated with an accessed location to determine if the contamination risk should be enforced. In some embodiments, the analysis component 112 can be configured to delete an associated contamination risk from a user profile. For example, the analysis component can be configured to delete the contamination risk from the user profile in response to expiration of an associated time period or, in another example, in response to access to a wash down room.

According to one embodiment, the CCP engine 104 can include an administration component 114 configured to accept user input regarding contamination risks and any respective duration. In some embodiments, the administration component 114 can be configured to display a user interface. The interface can include a display for associating locations with contamination risks. The interface can also be configured to provide for definition of locations subject to the contamination risk. In some embodiments, the interface can also be configured to require a duration for any defined contamination risk. In others, the duration is optional. For example, the system can set a default duration absent user specification. In another example, the duration can be infinite, for example, when the duration is not specified. An infinite duration effectively requires a person to visit a wash down room in order to clear their contamination state.

In some embodiments, the administration component 114 can be configured to accept identification of potential contaminants in a location and automatically identify contamination risks for other locations. For example, the materials used in an experiment can be entered into the administration component, and the materials can be matched against data for contamination risks with other materials present in other locations. Based on matching, the administration component can be configured to automatically define contamination risks between the matched locations. In some embodiments, the administration component 114 can automatically define contamination risks between materials in different locations. In some examples, the administration component can be configured to display automatically generated risks and request user approval prior to storing the defined contamination risks for use by the system.

In some embodiments, the CCP engine 104 itself can be configured to perform the functions and operations discussed with respect to the various components rather than requiring any specific component. As discussed, the CCP engine 104 and any components can be implemented on a CCPS (e.g., 100).

Figure 2:
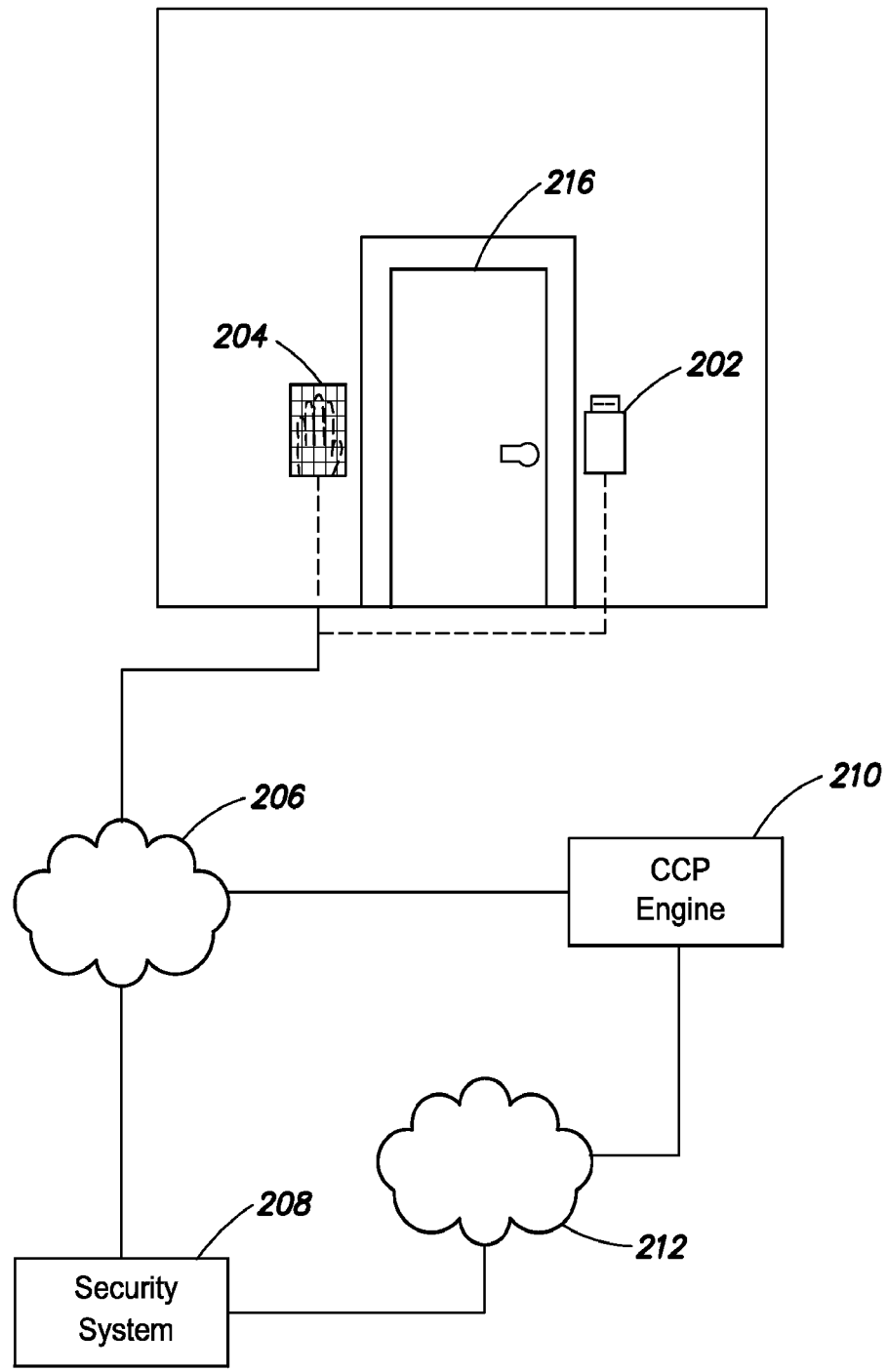
FIG. 2 is a block diagram of an example cross-contamination prevention system.

Shown in FIG. 2 is another embodiment of a CCPS 200, which can be configured to execute a CCP engine (e.g., 104) or perform the operations discussed with respect to the CCP engine 104 and any components. The CCPS 200 can include one or more access control devices (e.g., a badge reader 202 and biometric sensor 204) configured to receive an access credential from a person seeking entrance to a location (e.g., having a badge, RFID id, or biometric input, etc.). Other access control devices can be implemented, and include video recognition subsystems, RFID transmitters/receivers, wireless receivers, etc. In one embodiment, the access credential is communicated from access control devices (e.g., 202-204) over a network 206 to a security system 208. The security system 208 can be configured to determine if the person identified by the access credential is authorized to enter the location. If not, access can be denied by the security system 208, and for example, the door 216 remains barred.

As shown, the CCPS 200 can include existing security systems. In other embodiments, the CCPS 200 can receive communications from an existing security system to provide cross-contamination prevention techniques. In some embodiments, the CCPS and/or security system can be configured to track a person's location in a building (e.g., using location based services). The person's access credential can be stored on the system, and accessed as the person nears an access point. Thus, depending on the configuration, security input devices can be optional. Some location based services include GPS functions by smart phones, location tracking functions, magnetic, radio and/or wireless signals provided by badges or other id's, and can be implemented on a variety of mobile computer systems (including, e.g., smart phones, badges, authentication tokens, etc.). A CCPS and/or security system can incorporate one or more of such location tracking systems, and can include any combination of location tracking and/or access control devices to facilitate cross-contamination prevention.

In one example, the security system 208 can communicate with a CCP engine 210 via a communication network 212. According to some embodiments, even if a person is authorized to enter the location based on their access credential, the CCP engine 210 can still deny the person access. For example, once authorization to enter is determined, the CCP engine can evaluate any contamination risk posed by the person. If a contamination risk is identified, the CCP engine can deny access, and the door 216 remains barred. If no contamination risk is identified, the CCP engine 210 can communicate a control signal to the access control devices allowing access through the door 216. For example, the control signal communicated by the CCP engine can unlock or open the door 216.

In one embodiment, the security system remains responsible for permitting and/or denying access to the location. For example, the CCP engine 210 can communicate the result of the contamination evaluation to the security system 208. The security system 208 can be configured to allow access to the location, for example, by providing a control signal to unlock the door 216, in response to results provided by the CCP engine 210. The security system 208 can also be configured to deny access in response to an identified contamination risk communicated from the CCP engine 210. In further embodiments, the security system can be configured to supply information regarding the contamination risk to the person seeking entry. In one example, the security system can be configured to communicate a message regarding a contamination risk and reason for denying access. In another example, in response to a determination by the CCP engine, the security system can display an associated message regarding access. If, for example, a contamination risk is identified, the message can include information regarding a nearby wash down area to eliminate the contamination risk.

The security system 208 and the CCP engine 210 can be connected by a secure network connection 212. In some settings, the connection 212 can be physically separate from the network 206. In other embodiments, the connection 212 can be logically created over the existing network 206, for example, using a VPN or other communication security protocol.

Figure 3:
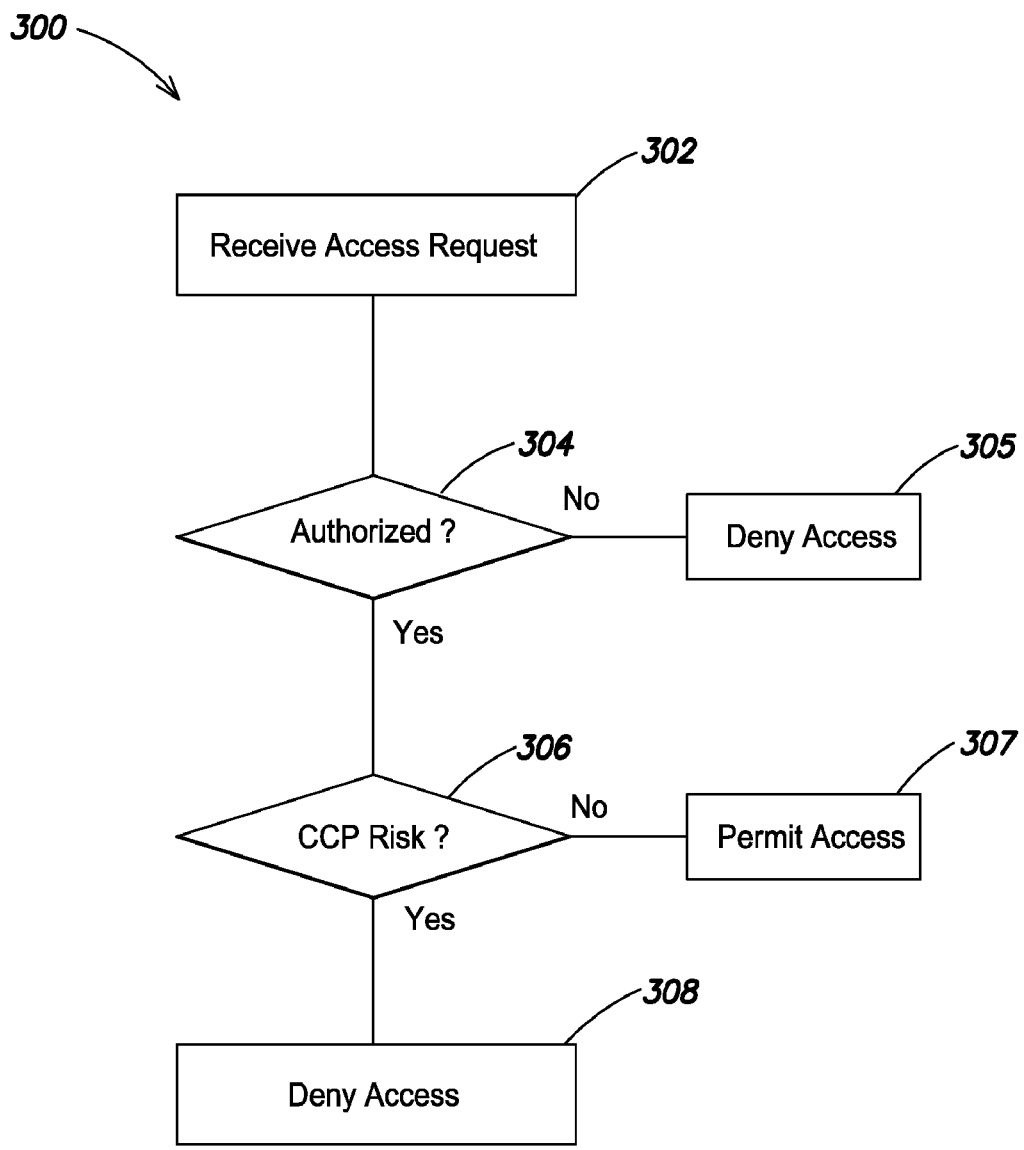
FIG. 3 is a flow diagram illustrating a process of controlling access responsive to cross-contamination risk.

Once access is granted to the person, the CCP engine 210 can be configured to track the accessed location for the person. For example, a user profile for the person can be associated with their access credential, and any contamination risk posed by the accessed location can be stored in the user profile. In other examples, the accessed location can be stored, and then used by the CCP engine to determine a contamination risk during subsequent access requests As discussed, a CCP engine and/or CCPS can be configured to execute a variety of processes to implement cross-contamination prevention. FIG. 3 illustrates an example process flow 300 for preventing cross-contamination. The process 300 begins at 302 with receiving an access request to a location. In one example, the access request and an associated access credential can be communicated from a security system responsible for managing personnel access to locations within a building. The access credential can be used by the security system to identify the requestor and determine any authorizations to enter the location.

In another example, the access request can be received from access control devices. The access control device can be configured to open and/or close access points within a building responsive to access authorization determined from the access request. In one embodiment, an employee places a badge proximate to a badge reader, to present an access request and associated identifying information encoded by the badge. At 304, a determination is made as to whether the requestor (e.g., employee) is authorized to enter the location based on the associated identifying information. If the requestor is not authorized 304 NO, process 300 can end with denying the requestor access at 305. Optionally, the requestor can be provided a message indicating that they are not authorized.

If the requestor is authorized, 304 YES, process 300 continues at 306 with a determination of any cross-contamination risk ("CC risk") associated with the access request. In one embodiment, determination of any cross-contamination risk at 306 includes retrieving prior location information associated with the requestor. For example, prior access requests can be stored, and the historical access information analyzed at 306 to determine any contamination risk. Prior locations can be associated with contamination risks. In some examples, the contamination risks can be defined against specific locations, and the check performed at 306 can determine if a contamination risk associated with a location previously visited by the requestor matches the current access request. If there is no matching risk, 306 NO, process 300 continues at 307 with permitting the requestor access to the location.

If there is a CC risk identified, 306 YES, process 300 continues with denying access to the requestor at 308. Optionally, the requestor can be provided information on why their access request was denied. In one example, the requestor can be informed of a cross-contamination risk, and further be provided information on proximate wash-down areas that will eliminate the cross-contamination risk.

In some embodiments, determination of CC risk at 306 can also include analysis of visits to wash-down areas. In one example, contamination risks associated with access to previous locations can be ignored if the requestor has visited a wash-down area after any location associated with a contamination risk. Some further embodiments of process 300 include consideration of any time periods associated with a contamination as part of the determination of CC risk at 306. For example, contamination risks can be defined by location and by an expiration date or time. The expiration date or time can define a time period past which the contamination risk should no longer be considered. Thus, contamination risks identified based on an access location can be ignored where an associated time period has elapsed. If a CC risk is ignored based on expiration of the time period, and no further risks are identified, 306 NO, process 300 can conclude with permitting the requestor access at 307.

Figure 4:
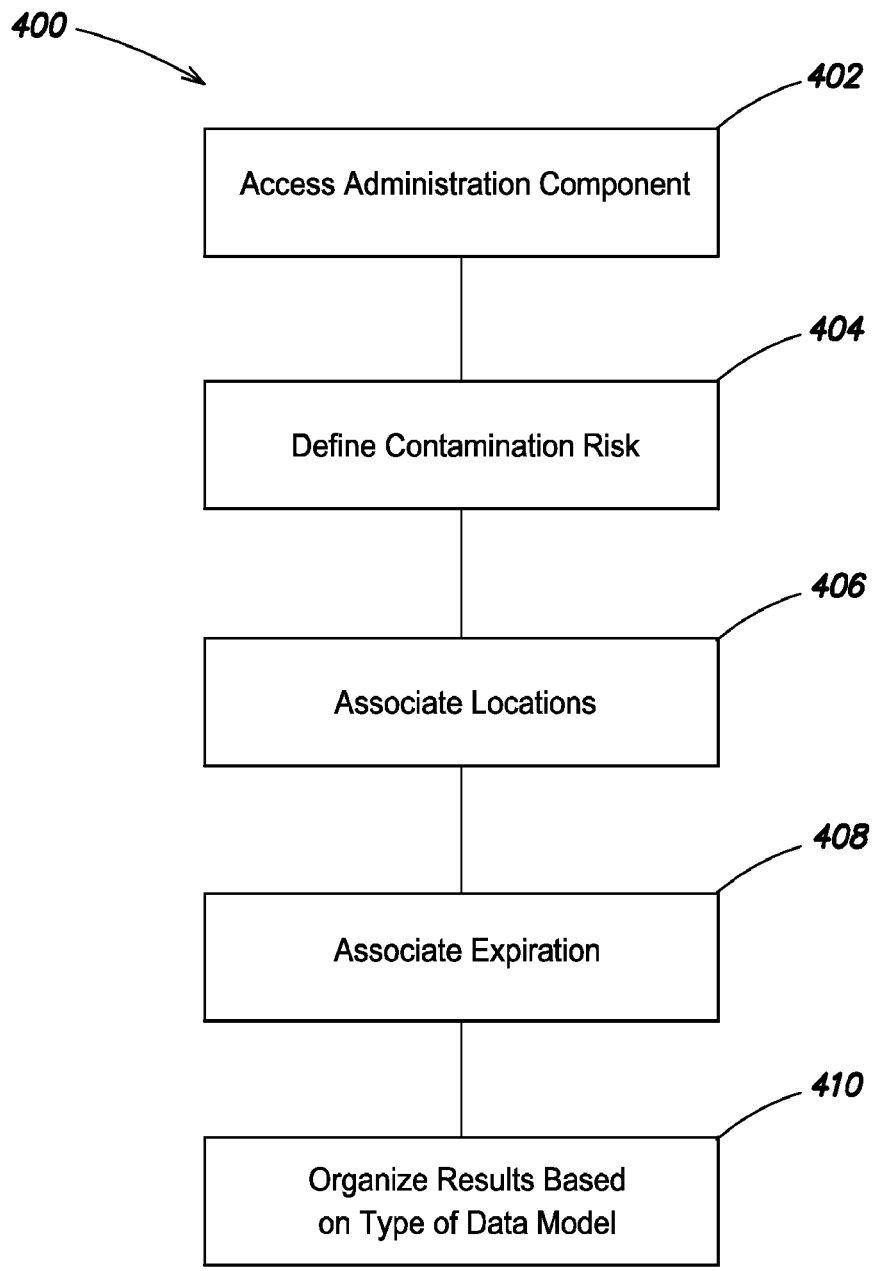
FIG. 4 is a flow diagram illustrating a process of defining cross-contamination risks.

FIG. 4 illustrates an example process flow 400 that can be executed by a CCP engine and/or CCPS. Process flow 400 provides for definition of cross-contamination risks. The process 400 begins at 402 with access to an administration component. Access to the administration component can include input (e.g., user name and passwords) to determined authorization to access the administration component. In some implementations, access to the administration component can be provided over a communication network (e.g., the internet). The communication network can be local to a building, a suite, a group of buildings, etc., including any location for which cross-contamination prevention is desired. In other examples, the communication network can be connected to remote locations, and access to the administration can be provided through a web page or web portal.

At 404, contamination risks can be defined. Defining the contamination risk for a location can include specifying a first location and identifying other locations that would be affected by the contamination risk posed by visiting the first location. For example, a user can define a contamination risk such that a visit to a laboratory location (e.g., Lab A), results in a contamination risk for another laboratory location (e.g., lab B). In one embodiment, a user can select from available locations in a particular environment (e.g., Labs A-Z), and for the selected location define target locations that would be affected. The user can select one or more locations that would be affected, and the selected locations are associated with the now defined contamination risk at 406, for example, in response to the user selecting "save" in a user interface. Optionally, the user may define a time period for a contamination risk at 408. Definition of the time period for the contamination risk results in the contamination risk expiring at the conclusion of the time period (e.g., measured from an access time to the location associated with the contamination risk). As discussed above, a contamination risk can also be eliminated by visiting a wash-down area during any period specified for a contamination risk.

In other embodiments, definition of the contamination risk at 404 can include identification of specific material(s) present at a location at 404. In one example, definition of the contamination risk can include searching a database of known contamination risks between materials. The database can include information on what materials are actually present in a specific environment, and risks can be automatically defined for a variety of locations at 404, for example, in response to entry of material present at a location. In one instance, material used in experiments for a lab are listed in a contamination database as having contamination risks associated with materials in another lab. Once a user enters the specific material in the administration component, contamination risks can be automatically identified/defined with their associated locations (e.g., at 404-406). In some embodiments, the database of contamination risks for materials can specify time periods for the contamination risks, and the contamination risk defined can optionally include an associated expiration (e.g., at 408).

Example Computer System

As discussed above with regard to FIG. 1, various aspects and functions described herein may be implemented as specialized hardware or software components executing in one or more computer systems. There are many examples of computer systems that are currently in use. These examples include, among others, network appliances, personal computers, workstations, mainframes, networked clients, servers, media servers, application servers, location systems, database servers and web servers. Other examples of computer systems may include mobile computing devices, such as cellular phones and personal digital assistants, and network equipment, such as load balancers, routers and switches. Further, aspects may be located on a single computer system or may be distributed among a plurality of computer systems connected to one or more communications networks.

For example, various aspects and functions may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Consequently, examples are not limited to executing on any particular system or group of systems. Further, aspects and functions may be implemented in software, hardware or firmware, or any combination thereof. Thus, aspects and functions may be implemented within methods, acts, systems, system elements and components using a variety of hardware and software configurations, and examples are not limited to any particular distributed architecture, network, or communication protocol.

Figure 5:
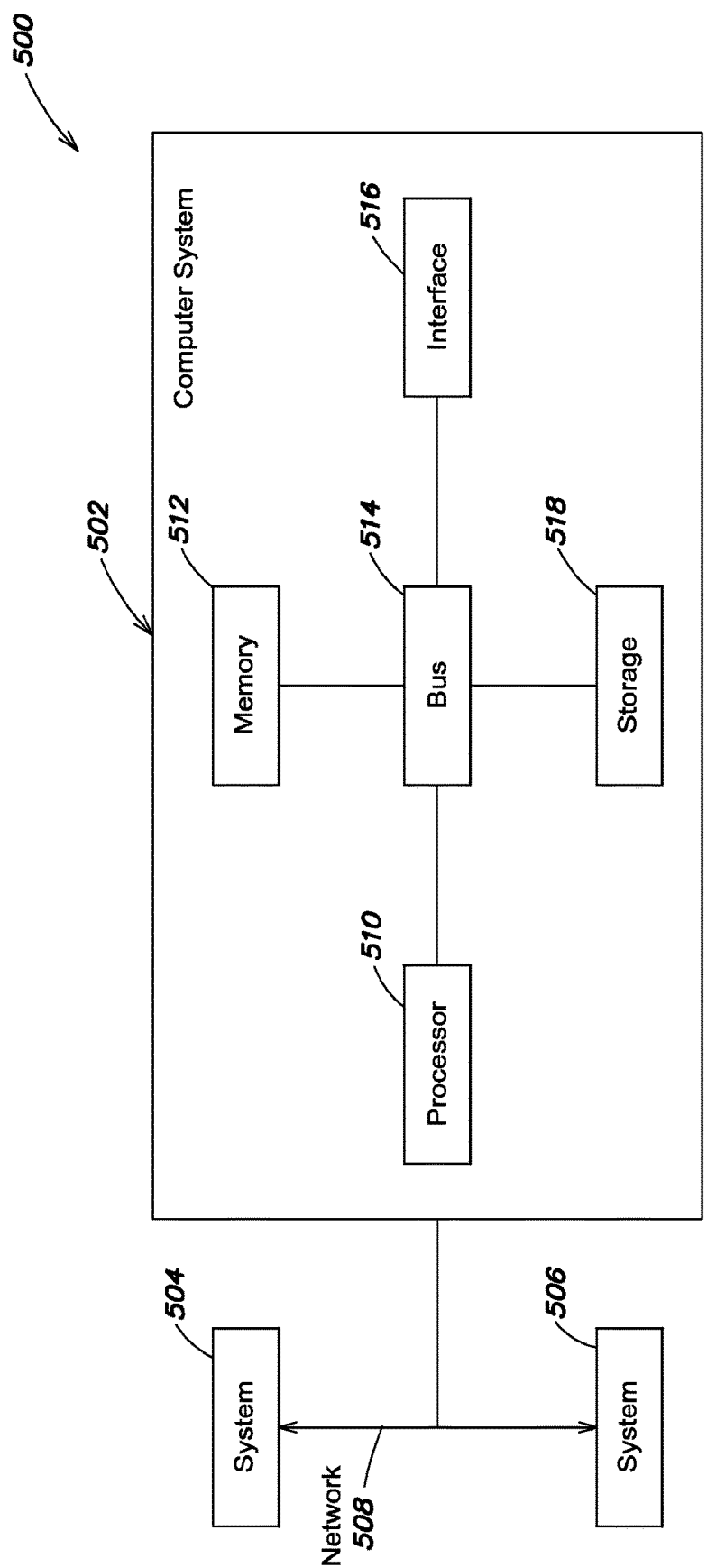
FIG. 5 a schematic diagram of an exemplary computer system that may be configured to perform processes and functions disclosed herein.

Referring to FIG. 5, there is illustrated a block diagram of a distributed computer system 500, in which various aspects and functions are practiced. As shown, the distributed computer system 500 includes one more computer systems that exchange information. More specifically, the distributed computer system 500 includes computer systems 502, 504 and 506. As shown, the computer systems 502, 504 and 506 are interconnected by, and may exchange data through, a communication network 508. For example, a CCPS and/or CCP engine can be implemented on 502, which communicates with a security system implemented on 504, which operate together to provide cross-contamination prevention functions as discussed herein. In other embodiments, the CCPS and/or CCP can include the security system and the functions performed can be implemented by 502 or distributed between 502-506.

In some embodiments, the network 508 may include any communication network through which computer systems may exchange data. To exchange data using the network 508, the computer systems 502, 504 and 506 and the network 508 may use various methods, protocols and standards, including, among others, Fibre Channel, Token Ring, Ethernet, Wireless Ethernet, Bluetooth, IP, IPV6, TCP/IP, UDP, DTN, HTTP, FTP, SNMP, SMS, MMS, SS7, JSON, SOAP, CORBA, REST and Web Services. To ensure data transfer is secure, the computer systems 502, 504 and 506 may transmit data via the network 508 using a variety of security measures including, for example, TLS, SSL or VPN. While the distributed computer system 500 illustrates three networked computer systems, the distributed computer system 500 is not so limited and may include any number of computer systems and computing devices, networked using any medium and communication protocol.

In some embodiments, access control devices can be implemented on a computer system (e.g., 502) and can include, in one example, a smart phone configured to communicate identifying information and/or an access credential to other computer systems (e.g., 504 and/or 506) which can be configured to determine, for example, access authority, CC risk, and manage physical access to a location.

As illustrated in FIG. 5, the computer system 502 includes a processor 510, a memory 512, a bus 514, an interface 516 and data storage 518. To implement at least some of the aspects, functions and processes disclosed herein, the processor 510 performs a series of instructions that result in manipulated data. The processor 510 may be any type of processor, multiprocessor or controller. Some exemplary processors include commercially available processors such as an Intel Xeon, Itanium, Core, Celeron, or Pentium processor, an AMD Opteron processor, a Sun UltraSPARC or IBM Power5+ processor and an IBM mainframe chip. The processor 510 is connected to other system components, including one or more memory devices 512, by the bus 514.

The memory 512 stores programs and data during operation of the computer system 502. Thus, the memory 512 may be a relatively high performance, volatile, random access memory such as a dynamic random access memory (DRAM) or static memory (SRAM). However, the memory 512 may include any device for storing data, such as a disk drive or other non-volatile storage device. Various examples may organize the memory 512 into particularized and, in some cases, unique structures to perform the functions disclosed herein. These data structures may be sized and organized to store values for particular data and types of data.

Components of the computer system 502 are coupled by an interconnection element such as the bus 514. The bus 514 may include one or more physical busses, for example, busses between components that are integrated within a same machine, but may include any communication coupling between system elements including specialized or standard computing bus technologies such as IDE, SCSI, PCI and InfiniBand. The bus 514 enables communications, such as data and instructions, to be exchanged between system components of the computer system 502.

The computer system 502 also includes one or more interface devices 516 such as input devices, output devices and combination input/output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 502 to exchange information and to communicate with external entities, such as users and other systems.

The data storage 518 includes a computer readable and writeable nonvolatile, or non-transitory, data storage medium in which instructions are stored that define a program or other object that is executed by the processor 510. The data storage 518 also may include information that is recorded, on or in, the medium, and that is processed by the processor 510 during execution of the program. More specifically, the information may be stored in one or more data structures specifically configured to conserve storage space or increase data exchange performance. The data storage can include specification of a location and any one or more other locations at which a CC risk would be present based on access to the location. Further, the data storage can includes time periods associated with any defined contamination risk.

The instructions stored in the date storage may be persistently stored as encoded signals, and the instructions may cause the processor 510 to perform any of the functions described herein. The medium may be, for example, optical disk, magnetic disk or flash memory, among other options. In operation, the processor 510 or some other controller causes data to be read from the nonvolatile recording medium into another memory, such as the memory 512, that allows for faster access to the information by the processor 510 than does the storage medium included in the data storage 518. The memory may be located in the data storage 518 or in the memory 512, however, the processor 510 manipulates the data within the memory, and then copies the data to the storage medium associated with the data storage 518 after processing is completed. A variety of components may manage data movement between the storage medium and other memory elements and examples are not limited to particular data management components. Further, examples are not limited to a particular memory system or data storage system.

Although the computer system 502 is shown by way of example as one type of computer system upon which various aspects and functions may be practiced, aspects and functions are not limited to being implemented on the computer system 502 as shown in FIG. 5. Various aspects and functions may be practiced on one or more computers having a different architectures or components than that shown in FIG. 5. For instance, the computer system 502 may include specially programmed, special-purpose hardware, such as an application-specific integrated circuit (ASIC) tailored to perform a particular operation disclosed herein. While another example may perform the same function using a grid of several general-purpose computing devices running MAC OS System X with Motorola PowerPC processors and several specialized computing devices running proprietary hardware and operating systems.

The computer system 502 may be a computer system including an operating system that manages at least a portion of the hardware elements included in the computer system 502. In some examples, a processor or controller, such as the processor 510, executes an operating system. Examples of a particular operating system that may be executed include a Windows-based operating system, such as, Windows NT, Windows 2000 (Windows ME), Windows XP, Windows Vista, Windows 7 or 8 operating systems, available from the Microsoft Corporation, a MAC OS System X operating system available from Apple Computer, one of many Linux-based operating system distributions, for example, the Enterprise Linux operating system available from Red Hat Inc., a Solaris operating system available from Sun Microsystems, or a UNIX operating systems available from various sources. Many other operating systems may be used, and examples are not limited to any particular operating system.

The processor 510 and operating system together define a computer platform for which application programs in high-level programming languages are written. These component applications may be executable, intermediate, bytecode or interpreted code which communicates over a communication network, for example, the Internet, using a communication protocol, for example, TCP/IP. Similarly, aspects may be implemented using an object-oriented programming language, such as .Net, SmallTalk, Java, C++, Ada, C# (C-Sharp), Objective C, or Javascript. Other object-oriented programming languages may also be used. Alternatively, functional, scripting, or logical programming languages may be used.

Additionally, various aspects and functions may be implemented in a non-programmed environment, for example, documents created in HTML, XML or other format that, when viewed in a window of a browser program, can render aspects of a graphical-user interface or perform other functions. For example, an administration component can render an interface in a browser to enable definition of contamination risks.

Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Accordingly, the functional components disclosed herein may include a wide variety of elements, e.g. specialized hardware, executable code, data structures or objects, that are configured to perform the functions described herein.

In some examples, the components disclosed herein may read parameters that affect the functions performed by the components. These parameters may be physically stored in any form of suitable memory including volatile memory (such as RAM) or nonvolatile memory (such as a magnetic hard drive). In addition, the parameters may be logically stored in a propriety data structure (such as a database or file defined by a user mode application) or in a commonly shared data structure (such as an application registry that is defined by an operating system). In addition, some examples provide for both system and user interfaces that allow external entities to modify the parameters and thereby configure the behavior of the components.

Various embodiments describe functions and operations performed with respect to tracking persons and managing access based on user profile information. In other embodiments, those functions and operations can be performed with respect to object associated with location information, through, for example, RFID devices. Each object can also be associated with a contamination risk, and entry can be denied by the system responsive to the system determining the object poses a contamination risk. For example, the system can analyze profiles associated with specific objects to track and analyze location and/or contamination state.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A system for cross-contamination prevention comprising: at least one processor operatively connected to a memory, the at least one processor when executing is configured to:

associate a first contaminant location with a first target location, the first contaminant location posing a risk to the first target location from a first contamination exposure, the first contamination exposure resulting from access to the first contaminant location:

associate a second contaminant location with a second target location, the second contaminant location posing a risk to the second target location from a second contamination exposure, the second contamination exposure resulting from access to the second contaminant location, the second contamination exposure being different from the first contamination exposure:

analyze an access request to a physical location;

identify a contamination risk posed by permitting access to the physical location, based on a determination whether the physical location is among the first target location or the second target location, and based on first contamination exposure associated with prior access to the first contamination location or second contamination exposure associated with prior access to the second contamination location; and restrict access to the physical location in response to identifying the contamination risk.

2. The system according to claim 1, further comprising a storage subsystem configured to store contamination risks associated with a plurality of target locations.

3. The system according to claim 2, wherein the storage subsystem is configured to associate information on at east one contamination exposure with a person based on access to at least one of contamination location.

4. The system according to claim 2, wherein the storage subsystem is configured to define a time period associated contamination risk.

5. The system according to claim 1, further comprising an access control subsystem configured to receive an access credential from a person seeking access to the physical location.

6. The system according to claim 5, wherein the at least one processor is configured to determine authorization to enter the physical location responsive to the access credential.

7. The system according to claim 5, wherein the at least one processor is configured to determine the first contamination exposure associated with prior access to the first contamination location associated with an access request responsive to receiving the access credential.

8. The system according to claim 7, wherein the at least one processor is configured to communicate a control message, to the access control subsystem to restrict access to the physical location.

9. The system according to claim 1, wherein identifying the contamination risk posed by permitting access includes changing one or more contamination risks responsive to access to a sterilization location.

10. The system according to claim 1, wherein identifying the contamination risk posed by permitting access includes changing one or more contamination risks responsive to a time period associated with a respective one of the one or more contamination risks.

11. A method for cross-contamination prevention comprising:

associating a first contaminant location with a first target location, the first contaminant location posing a risk to the first target location from a first contamination exposure, the first contamination exposure resulting from access to the first contaminant location:

associating a second contaminant location with a second target location, the second contaminant location posing a risk to the second target location from a second contamination exposure, the second contamination exposure resulting from access to the second contaminant location, the second contamination exposure being different from the first contamination exposure;

analyzing, by a computer system, an access request to a physical location;

identifying, by the computer system, a contamination risk posed by permitting access, based on a determination whether the physical location is among the first target location or the second target location, and based on first contamination exposure associated with prior access to the first contamination location or second contamination exposure associated with prior access to the second contamination location; and restricting, by the computer system, access to the physical location in response to identifying the contamination risk.

12. The method according to claim 11, further comprising storing, by the computer system, contamination risks associated with a plurality of target locations.

13. The method according to claim 12, further comprising associating information on at least one contamination exposure with a person based on access to at least one of contamination location.

14. The method according to claim 12, further comprising defining a time period associated with a respective contamination risk.

15. The method according to claim 11, further comprising receiving an access credential from a person seeking access to the physical location.

16. The method according to claim 15, further comprising determining authorization to enter the physical location responsive to the access credential.

17. The method according to claim 15, further comprising determining the first contamination exposure associated with prior access to the first contamination location associated with an access request responsive to receiving the access credential.

18. The method according to claim 11, wherein identifying the contamination risk posed by permitting access includes changing one or more contamination risks responsive to access to a sterilization location.

19. The method according to claim 11, wherein identifying the contamination risk posed by permitting access includes changing one or more contamination risks based on a time period associated with a respective one of the one or more contamination risks.

20. A non-transitory computer readable medium having stored thereon sequences of instruction for cross-contamination prevention including instructions that will cause at least one processor of a computer system to:

associate a first contaminant location with a first target location, the first contaminant location posing a risk to the first target location from a first contamination exposure, the first contamination exposure resulting from access to the first contaminant location:

associate a second contaminant location with a second target location, the second contaminant location posing a risk to the second target location from a second contamination exposure, the second contamination exposure resulting from access to the second contaminant location, the second contamination exposure being different from the first contamination exposure:

analyze an access request to a physical location;

identify a contamination risk posed by permitting access, based on a determination whether the physical location is among the first target location or the second target location, and based on first contamination exposure associated with prior access to the first contamination location or second contamination exposure associated with prior access to the second contamination location; and restrict access to the physical location in response to identifying the contamination risk.

* * * * *